United States Patent
Darteil et al.

(10) Patent No.: US 10,117,856 B2
(45) Date of Patent: *Nov. 6, 2018

(54) METHODS OF TREATMENT FOR CHOLESTATIC AND FIBROTIC DISEASES

(71) Applicant: Genfit, Loos (FR)

(72) Inventors: Raphael Darteil, Lille (FR); Robert Walczak, Lille (FR); Carole Belanger, Bondues (FR); Emilie Negro, Lille (FR); Pierre Daubersies, Vitry en Artois (FR); Philippe Delataille, Ronchin (FR)

(73) Assignee: Genfit, Loos (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/841,981

(22) Filed: Dec. 14, 2017

(65) Prior Publication Data

US 2018/0092885 A1 Apr. 5, 2018

Related U.S. Application Data

(63) Continuation of application No. 15/457,158, filed on Mar. 13, 2017.

(30) Foreign Application Priority Data

Apr. 11, 2016 (EP) .................................... 16305425

(51) Int. Cl.
*A61K 45/06* (2006.01)
*A61K 31/426* (2006.01)

(52) U.S. Cl.
CPC ............ *A61K 31/426* (2013.01); *A61K 45/06* (2013.01)

(58) Field of Classification Search
CPC ..................................................... A61K 45/06
See application file for complete search history.

(56) References Cited

U.S. PATENT DOCUMENTS

| | | | |
|---|---|---|---|
| 3,950,351 | A | 4/1976 | Rossignol et al. |
| 3,957,812 | A | 5/1976 | Rossignol et al. |
| 5,886,013 | A | 3/1999 | Rossignol |
| 5,935,591 | A | 8/1999 | Rossignol et al. |
| 5,965,590 | A | 10/1999 | Rossignol |
| 5,968,961 | A | 10/1999 | Rossignol |
| 6,020,353 | A | 2/2000 | Rossignol |
| 6,114,365 | A | 9/2000 | Pevarello et al. |
| 6,117,894 | A | 9/2000 | Rossignol |
| 6,784,198 | B1 | 8/2004 | Pevarello et al. |

(Continued)

FOREIGN PATENT DOCUMENTS

| | | |
|---|---|---|
| EP | 1354603 | 10/2003 |
| EP | 16305425.7 | 10/2017 |

(Continued)

OTHER PUBLICATIONS

Leask, A et al. "TGF-β signaling and the fibrotic response" The FASEB Journal, 2004, pp. 816-827, vol. 18, No. 7.

(Continued)

*Primary Examiner* — Benjamin J Packard
(74) *Attorney, Agent, or Firm* — Leason Ellis LLP

(57) ABSTRACT

The present invention relates to the compound [2-[(5-nitro-1,3-thiazol-2-yl)carbamoyl]phenyl]ethanoate (Nitazoxanide) or 2-hydroxy-N-(5-nitro-2-thiazolyl)benzamide (Tizoxanide) for treating cholestatic and fibrotic diseases.

10 Claims, 4 Drawing Sheets

Figure 1:
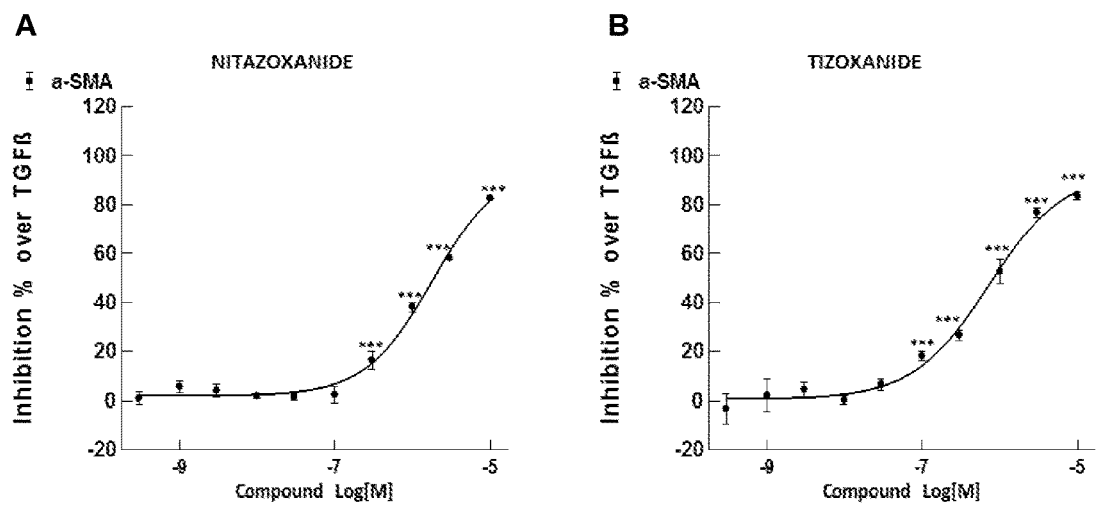

Specification includes a Sequence Listing.

(56) References Cited

U.S. PATENT DOCUMENTS

| | | | |
|---|---|---|---|
| 7,285,567 | B2 | 10/2007 | Rossignol |
| 7,550,493 | B2 | 6/2009 | Rossignol |
| 7,645,783 | B2 | 1/2010 | Rossignol |
| 8,124,632 | B2 | 2/2012 | Rossignol et al. |
| 8,524,478 | B2 | 9/2013 | Park et al. |
| 8,633,230 | B2 | 1/2014 | Rossignol |
| 8,772,502 | B2 | 7/2014 | Semple |
| 8,846,727 | B2 | 9/2014 | Rossignol et al. |
| 9,023,877 | B2 | 5/2015 | Rossignol et al. |
| 9,107,913 | B2 | 8/2015 | Rossignol |
| 2005/0004120 | A1 | 1/2005 | Pevarello et al. |
| 2010/0015093 | A1 | 1/2010 | Einav et al. |
| 2011/0244027 | A1 | 10/2011 | Chu et al. |
| 2012/0053210 | A1 | 3/2012 | Whitten |
| 2012/0294831 | A1 | 11/2012 | Pevarello et al. |
| 2014/0256745 | A1 | 9/2014 | Cao |
| 2016/0008320 | A1 | 1/2016 | Froehner |
| 2017/0290812 | A1 | 10/2017 | Darteil et al. |
| 2017/0290813 | A1 | 10/2017 | Walczak et al. |
| 2017/0290814 | A1 | 10/2017 | Dubernet et al. |

FOREIGN PATENT DOCUMENTS

| | | |
|---|---|---|
| EP | 16305426.5 | 10/2017 |
| EP | 16305427.3 | 10/2017 |
| EP | 16305428.1 | 10/2017 |
| WO | 2005026137 | 3/2005 |
| WO | 2007059359 | 5/2007 |
| WO | 2007081974 | 7/2007 |
| WO | 2007087427 | 8/2007 |
| WO | 2007130075 | 11/2007 |
| WO | 2008040967 | 4/2008 |
| WO | 2009023509 | 2/2009 |
| WO | 2009039246 | 3/2009 |
| WO | 2009039248 | 3/2009 |
| WO | 2010121128 | 10/2010 |
| WO | 2011060408 | 5/2011 |
| WO | 2011140190 | 11/2011 |
| WO | 2011140296 | 11/2011 |
| WO | 2012013716 | 2/2012 |
| WO | 2012158552 | 5/2012 |
| WO | 2012118712 | 9/2012 |
| WO | 2013082469 | 6/2013 |
| WO | 2014036528 | 3/2014 |
| WO | 2014059333 | 4/2014 |
| WO | 2016077420 | 5/2016 |
| WO | 2016210247 | 12/2016 |
| WO | 2017178172 | 10/2017 |
| WO | 2017178173 | 10/2017 |
| WO | 2017178174 | 10/2017 |

OTHER PUBLICATIONS

Leask, A "TGF-β, cardiac fibroblasts, and the fibrotic response" Cardiovascular Research, 2007, pp. 207-212, vol. 74, No. 2.
Rosenbloom, J. et al. "Strategies for anti-fibrotic therapies" Biochimica et Biophysica Acta, 2013, pp. 1088-1103, vol. 1832, No. 7.
European Search Report dated Jun. 22, 2016 corresponding to European Application No. 16305426.5; 6 pages.
Database Registry, Chemical Abstracts Service, Columbus,Ohio, US; Oct. 22, 2010 (Oct. 22, 2010), retrieved from STN, database accession No. RN: 1246819-17-9, 1246817-56-0.
Pankuch et al: "Activities of tizoxanide and nitazoxanide compared to those of five other thiazolides and three other agents against anaerobic species", Antimicrobial Agents and Chemotherapy, vol. 50, No. 3, Mar. 2006, pp. 1112-1117.
European Search Report dated Sep. 28, 2016 corresponding to European Application No. 16305425.7; 7 pages.
Basu et al: "Effects of triple-drug therapy with nitazoxanide, high-dose ribavirin and peginterferon-[alpha]-2a in patients with chronic hepatitis C", Hepatology Research, vol. 43, No. 6, 2013, pp. 589-595.
Korba et al: "Nitazoxanide, tizoxanide and other thiazolides are potent inhibitors of hepatitis B virus and hepatitis C virus replication", Antiviral Research, vol. 77, No. 1, 2008, pp. 56-63.
International Search Report and Written Opinion dated Jun. 2, 2017 corresponding to International Patent Application No. PCT/EP2017/055880; 13 pages.
Blanchard et al, Giardiasis and Cryptosporidiosis—Recent Literature with a Focus on Nitazoxanide, Pediatrics & Therapeutics, vol. 5, No. 4, 2015: 265.
International Search Report and Written Opinion dated Jun. 20, 2017 corresponding to International Patent Application No. PCT/EP2017/055881; 27 pages.
U.S. Appl. No. 15/644,637, Reissue of U.S. Pat. No. 9,107,913.
González-Casas,et al, [Chronic C hepatitis genotype 4], Med Clin (Barc), 2011, 137(1), 31-5; Abstract.
Shehab HM et al, Nitazoxanide plus pegylated interferon and ribavirin in the treatment of genotype 4 chronic hepatitis C, a randomized controlled trial, Liver Int, 2013, 34, (2), 259-65.
Broekhuysen, J. et al. "Nitazoxanide: pharmacokinetics and metabolism in man" International Journal of Clinical Pharmacology and Therapeutics, 2000, pp. 387-394, vol. 38, No. 8.
Chong, L -W. et al. "Fluvastatin attenuates hepatic steatosis-induced fibrogenesis in rats through inhibiting paracrine effect of hepatocyte on hepatic stellate cells" BMC Gastroenteroloy, 2015, pp. 1-13, vol. 15, No. 22.
De Carvalho, L. P. S. et al. "Nitazoxanide Disrupts Membrane Potential and Intrabacterial pH Homeostasis of Mycobacterium tuberculosis" ACS Medicinal Chemistry Letters, 2011, pp. 849-854, vol. 2.
Di Santo, N. et al. "A functional perspective of nitazoxanide as a potential anticancer drug", Mutation Research, 2014, pp. 16-21, vol. 768.
Dubreuil, L. et al. "In Vitro Evaluation of Activities of Nitazoxanlde and Tizoxanide against Anaerobes and Aerobic Organisms Antimicrobial Agents and Chemotherapy", Oct. 1996, pp. 2266-2270, vol. 40, No. 10.
Fox, L. M. et al. "Nitazoxanide: A New Thiazolide Antiparasitic Agent" Reviews of Anti-Infective Agents, Apr. 15, 2005, pp. 1173-1180, vol. 40.
Hemphill, A. et al. "Nitazoxanide, a broad-spectrum thiazolide anti-infective agent for the treatment of gastrointestinal infections", Expert Opinion Pharmacotherapy, 2006, pp. 1-12, vol. 7, No. 7.
Hoffman, P. S. et al. "Antiparasitic Drug Nitazoxanide Inhibits the Pyruvate Oxidoreductases of Helicobacter pylori, Selected Anaerobic Bacteria and Parasites, and Campylobacter jejuni", Antimicrobial Agents and Chemotherapy, Mar. 2007, pp. 868-876, vol. 51, No. 3.
Kavalipati, N. et al. "Pleiotropic effects of statins" Indian Journal of Endocrinology and Metabolism, Sep.-Oct. 2015, pp. 554-562, vol. 19, No. 5.
Kendall, R. T. et al. "Fibroblasts in fibrosis: novel roles and mediators" Frontiers in Pharmacology, Ma 27, 2014, pp. 1-13, vol. 5, Article 123.
Kikelj, D. et al. "Product Class 17: Thiazoles" Science of Synthesis 4. 8, 2017, pp. 627-631, Section 11.17.
Marrone, G. et al. "KLF2 exerts antifibrotic and vasoprotective effects in cirrhotic rat livers: behind the molecular mechanisms of statins" Gut, 2015, pp. 1434-1443, vol. 64.
McFarlane, S. I. et al. "Clinical Review 145: Pleiotropic Effects of Statins: Lipid Reduction and Beyond" The Journal of Clinical Endocrinology & Metabolism, Apr. 2002, pp. 1451-1458, vol. 87, No. 4.
McKenney, J. M. "Pharmacologic Characteristics of Statins" Clinical Cardiology, 2003, pp. 111-32-111-38, vol. 26, Su I. III.
Megraud, F. et al. "Nitazoxanide, a Potential Drug for Eradication of Helicobacter pylori with No Cross-Resistance to Metronidazole" Antimicrobial Agents and Chemotherapy, Nov. 1998, pp. 2836-2840, vol. 42, No. 11.
Miyaki, T. et al. "Pitavastatin inhibits hepatic steatosis and fibrosis in non-alcoholic steatohepatitis model rats" Hepatology Research, 2011, pp. 375-385, vol. 41.

(56) References Cited

OTHER PUBLICATIONS

Rombouts, K et al. "Effect of Hmg-CoA reductase inhibitors on proliferation and protein synthesis by rat hepatic stellate cells" Journal of Hepatology, 2003, pp. 564-572, vol. 38.
Rossignol, J. F. "Nitazoxanide: A first-in-class broad-spectrum antiviral agent" Antiviral Research, 2014, pp. 94-103, vol. 110.
Rossignol, J. F. et al. "Brief Communication—Nitazoxanide in the Treatment of Taenia Saginata and Hymenolepis Nana Infections" American Journal of Tropical Medicine and Hygiene, 1984, pp. 511-512, vol. 33, No. 3.
Sebastian et al. "Chronic Hepatitis C and Liver Fibrosis". World J Gastroenterol. Aug. 28, 2014; 20(32): 11033-11053.
Stachulski, A. V. et al. "Synthesis and pre-clinical studies of new amino-acid ester thiazolide prodrugs" European Journal of Medicinal Chemistry, 2017, pp. 154-159, vol. 126.
Vere et al. "Statins in the Treatment of Hepatitis C". Hepatitis Monthly, 2012; 12(6):369-371.
Wang, W. et al. "Simvastatin Ameliorates Liver Fibrosis via Mediating Nitric Oxide Synthase in Rats with Non-Alcoholic Steatohepatitis-Related Liver Fibrosis" PLOS One, Oct. 2013, pp. 1-11, vol. 8, No. 10.
Watts, K. L. et al. "Simvastatin Inhibits Growth Factor Expression and Modulates Profibrogenic Markers in Lung Fibroblasts" American Journal of Respiratory Cell and Molecular Biology, 2005, pp. 290-300, vol. 32.
Yeganeh, B. et al. "Targeting the mevalonate cascade as a new therapeutic approach in heart disease, cancer and pulmonary disease" Pharmacology and Therapeutics, 2014, pp. 87-110, vol. 143.
Zhou, Q. et al. "Statins and Cardiovascular Diseases: From Cholesterol Lowering to Pleiotropy" Current Pharmaceutical Design, 2009, pp. 1-22, vol. 15, No. 5.
Zhu, B. et al. "Atorvastatin Attenuates Bleomycin-Induced Pulmonary Fibrosis via Suppressing iNOS Expression and the CTGF (CCN2)/ERK Signaling Pathway" Internal Journal of Molecular Science, Dec. 16, 2013, pp. 24476-24491, vol. 14, No. 12.
U.S. Appl. No. 15/958,713, filed Apr. 20, 2018.
European Search Report dated Sep. 28, 2016 corresponding to European Application No. 16305427.3; 7 pages.
International Search Report and Written Opinion dated May 23, 2017 corresponding to International Patent Application No. PCT/EP2017/055878; 10 pages.

SEQUENCE LISTING

```
<160> NUMBER OF SEQ ID NOS: 4

<210> SEQ ID NO 1
<211> LENGTH: 25
<212> TYPE: DNA
<213> ORGANISM: artificial
<220> FEATURE:
<223> OTHER INFORMATION: primer

<400> SEQUENCE: 1
catgctcaac atctcccct tctcc                              25

<210> SEQ ID NO 2
<211> LENGTH: 25
<212> TYPE: DNA
<213> ORGANISM: artificial
<220> FEATURE:
<223> OTHER INFORMATION: primer

<400> SEQUENCE: 2
gggaaggtgt aatccgtctc cacag                             25
```

```
<210> SEQ ID NO 3
<211> LENGTH: 20
<212> TYPE: DNA
<213> ORGANISM: artificial
<220> FEATURE:
<223> OTHER INFORMATION: primer

<400> SEQUENCE: 3
aggcgaacaa ggtgacagag                                               20

<210> SEQ ID NO 4
<211> LENGTH: 19
<212> TYPE: DNA
<213> ORGANISM: artificial
<220> FEATURE:
<223> OTHER INFORMATION: primer

<400> SEQUENCE: 4
gccaggagaa ccagcagag                                                19
```

METHODS OF TREATMENT FOR CHOLESTATIC AND FIBROTIC DISEASES

SEQUENCE LISTING

The Instant application contains a Sequence Listing which has been filed electronically in ASCII format and is hereby incorporated by reference in its entirety. Said ASCII copy, created on Dec. 14, 2017, is named "11211_006409-US2_ST25.txt" and is 1 KB in size.

TECHNICAL FIELD

The present invention relates to the field of medicine, in particular to the treatment of cholestatic or fibrotic diseases.

BACKGROUND

Abnormal and exaggerated deposition of extracellular matrix is the hallmark of all fibrotic diseases, including liver, pulmonary, kidney or cardiac fibrosis. The spectrum of affected organs, the progressive nature of the fibrotic process, the large number of affected persons, and the absence of effective treatment pose an enormous challenge when treating fibrotic diseases.

In an attempt to propose new therapeutic strategies for the treatment of fibrotic diseases, the inventors found that the compound 2-[(5-nitro-1,3-triazol-2-yl)carbamoyl]phenyl)ethanoate (Nitazoxanide or NTZ), a synthetic antiprotozoal agent, also shows potent antifibrotic properties. Moreover, the evaluation of NTZ in a liver injury model revealed its capacity to reduce circulating bile acid concentration, thus reflecting its potential to treat both cholestatic (such as PBC and PSC) and fibrotic diseases.

NTZ, first described in 1975 (Rossignol and Cavier, 1975), was shown to be highly effective against anaerobic protozoa, helminths, and a wide spectrum of microbes including both anaerobic and aerobic bacteria (Rossignol and Malsonneuve, 1984: Dubreull, Houcke et al., 1996; Megraudd, Occhlalini et al., 1998; Fox and Saravolatz. 2005; Pankuch and Appelbaum. 2006: Finegold, Molitoris et al., 2009). It was first studied in humans for the treatment of intestinal cestodes (Rossignol and Maisonneuve, 1984) and it is now licensed in the United States (Alinia®, Romark laboratories) for the treatment of diarrhea caused by the protozoan parasites *Crystosporidium parvum* and *Giardia intestinalis*. NTZ has also been widely commercialized in Latin America and in India where it is indicated for treating a broad spectrum of intestinal parasitic infections (Hemphill, Mueller et al., 2006). The proposed mechanism of action by which NTZ exerts its antiparasitic activity is through the inhibition of pyruvate:ferredoxin oxidoreductase (PFOR) enzyme-dependent electron transfer reactions that are essential for anaerobic metabolism (Hoffman, Sisson et al., 2007). NTZ also exhibits activity against *Mycobacterium tuberculosis*, which does not possess a homolog of PFOR, thus suggesting an alternative mechanism of action. Indeed, it was shown that NTZ can also act as an uncoupler disrupting membrane potential and intra-organism pH homeostasis (de Carvalho, Darby et al., 2011).

The pharmacological effects of NTZ are not restricted to its antiparasitic activities and in recent years, several studies revealed that NTZ can also confer antiviral activity (Di Santo and Ehrisman, 2014; Rossignol, 2014). NTZ interferes with the viral replication by diverse ways including a blockade in the maturation of hemagglutinin (influenza) or VP7 (rotavirus) proteins, or the activation of the protein PKR involved in the innate immune response (for a review, see (Rossignol, 2014)). NTZ was also shown to have broad anticancer properties by interfering with crucial metabolic and prodeath signaling pathways (Di Santo and Ehrisman, 2014)

In this invention, using a phenotypic screening assay to identify potential antifibrotic agents, it was discovered that NTZ or its active metabolite Tizoxanide (or TZ) interferes with the activation of hepatic stellate cells (HSC), which play a key role in the development of hepatic fibrosis. This effect was totally unexpected in view of the properties previously reported for these molecules. Moreover, NTZ and TZ were shown to interfere with the activation of stimulated fibroblasts derived from other organs such as heart, lung and intestines. The antifibrotic properties of NTZ was further confirmed in a preclinical model of liver disease (CDAAc diet-induced NASH) by showing significant reduced levels of hepatic collagen and fibrosis. In addition to its antifibrotic activity, NTZ was also shown to reduce circulating bile acid concentration in a CCl4-induced liver injury model. NTZ and TZ thus appear as compounds of interest for the treatment of cholestatic diseases and diverse types of fibrotic diseases.

SUMMARY OF INVENTION

The present invention relates to compound (2-[(5-nitro-1,3-thiazol-2-yl)carbamoyl]phenyl)ethanoate (Nitazoxanide) or its active metabolites 2-hydroxy-N-(5-nitro-2-thiazolyl)benzamide (Tizoxanide), or Tizoxanide glucuronide (TZG), or a pharmaceutically acceptable salt thereof, for use in a method for the treatment of a cholestatic or fibrotic disease.

In a particular embodiment, the fibrotic disorder is selected in the group consisting of liver, gut, kidney, skin, epidermis, endodermis, muscle, tendon, cartilage, heart, pancreas, lung, uterus, nervous system, testis, penis, ovary, adrenal gland, artery, vein, colon, intestine (e.g. small intestine), biliary tract, soft tissue (e.g. mediastinum or retroperitoneum), bone marrow, joint, eye and stomach fibrosis. In a further particular embodiment, the fibrotic disorder is selected in the group consisting of liver, kidney, skin, epidermis, endodermis, muscle, tendon, cartilage, heart, pancreas, lung, uterus, nervous system, testis, ovary, adrenal gland, artery, vein, colon, intestine (e.g. small intestine), biliary tract, soft tissue (e.g. mediastinum or retroperitoneum), bone marrow, joint and stomach fibrosis. In a further particular embodiment, the fibrotic disorder is selected in the group consisting of liver, gut, lung, heart, kidney, muscle, skin, soft tissue, bone marrow, intestinal, and joint fibrosis. In yet another embodiment the fibrotic disorder is selected in the group consisting of non-alcoholic steatohepatitis (NASH), pulmonary fibrosis, idiopathic pulmonary fibrosis, skin fibrosis, eye fibrosis (such as capsular fibrosis), endomyocardial fibrosis, mediastinal fibrosis, myelofibrosis, retroperitoneal fibrosis, progressive massive fibrosis (a complication of coal workers' pneumoconiosis), proliferative fibrosis, neoplastic fibrosis, lung fibrosis consecutive to chronic inflammatory airway disease (COPD, asthma, emphysema, smoker's lung, tuberculosis), alcohol or drug-induced liver fibrosis, liver cirrhosis, infection-induced liver fibrosis, radiation or chemotherapeutic-induced fibrosis, nephrogenic systemic fibrosis, Crohn's disease, ulcerative colitis, keloid, old myocardial infarction, scleroderma/systemic sclerosis, arthrofibrosis, some forms of adhesive capsulitis, chronic fibrosing cholangiopathies such as Primary Sclerosing Cholangitis (PSC), Primary Biliary Cholangitis (PBC), biliary atresia, familial intrahepatic cholestasis type 3 (PFIC3), peri-implantational fibrosis and asbestosis.

According to a particular embodiment of the invention, the cholestestatic disease is selected in the group consisting of primary biliary cholangitis (PBC), primary sclerosing cholangitis (PSC), Intrahepatic Cholestasis of Pregnancy, Progressive Familial Intrahepatic Cholestasis, Biliary atresia, Cholelithiasis, Infectious Cholangitis, Cholangitis associated with Langerhans cell histiocytosis, Alagille syndrome, Nonsyndromic ductal paucity, Drug-induced cholestasis, and Total parenteral nutrition-associated cholestasis. In a particular embodiment, the cholestatic disease is PBC.

According to another aspect, the invention relates to a pharmaceutical composition comprising a compound selected from NTZ or TZ(G), or a pharmaceutically acceptable salt of NTZ or TZ(G), for use in a method for treating a cholestatic or fibrotic disorder, wherein said compound(s) is(are) the only active ingredient(s) in the composition.

According to another aspect, the invention relates to the compound or the pharmaceutical composition as defined above, for use in the treatment of a fibrotic disorder in combination with at least one therapeutically active agent with known antifibrotic activity selected from pirfenidone or receptor tyrosine kinase inhibitors (RTKIs) such as Nintedanib, Sorafenib and other RTKIs. or angiotensin II (AT1) receptor blockers, or CTGF inhibitor, or any antifibrotic compound susceptible to interfere with the TGFβ- and BMP-activated pathways including activators of the latent TGFβ complex such as MMP2. MMP9, THBS1 or cell-surface integrins. TGFβ receptors type I (TGFBRI) or type II (TGFBRII) and their ligands such as TGFβ. Activin, inhibin, Nodal, anti-Müllerian hormone, GDFs or BMPs, auxiliary co-receptors (also known as type III receptors), or components of the SMAD-dependent canonical pathway including regulatory or inhibitory SMAD proteins, or members of the SMAD-independent or non-canonical pathways including various branches of MAPK signaling, TAK1, Rho-like GTPase signaling pathways, phosphatidylinositol-3 kinase/AKT pathways. TGFβ-induced EMT process, or canonical and non-canonical Hedgehog signaling pathways including Hh ligands or target genes, or any members of the WNT, or Notch pathways which are susceptible to influence TGFβ signaling.

The invention further relates to the compound or pharmaceutical composition as defined above, for use in combination with at least one therapeutically active agent selected from JAK/STAT inhibitors, other anti-inflammatory agents and/or immunosuppressant agents.

According to a particular embodiment, the therapeutically active agent is selected from glucocorticoids, NSAIDS, cyclophosphamide, nitrosoureas, folic acid analogs, purine analogs, pyrimidine analogs, methotrexate, azathioprine, mercaptopurine, ciclosporin, myriocin, tacrolimus, sirolimus, mycophenolic acid derivatives, fingolimod and other sphingosine-1-phosphate receptor modulators, monoclonal and/or polyclonal antibodies against such targets as proinflammatory cytokines and proinflammatory cytokine receptors, T-cell receptor, Integrins.

The Invention further relates to a pharmaceutical composition comprising
NTZ or a pharmaceutically acceptable salt of NTZ; and
TZ(G), or a pharmaceutically acceptable salt of TZ(G).
The invention also relates to a kit-of-parts comprising:
NTZ or a pharmaceutically acceptable salt of NTZ; and
TZ(G) or a pharmaceutically acceptable salt of TZ(G).

According to a particular embodiment, in each aspects and embodiments described herein, NTZ or TZ, or a pharmaceutically acceptable salt of NTZ or TZ is used.

DESCRIPTION OF THE FIGURES AND TABLES

Abbreviations Used in the Figures, in the Tables, and in the Text

α-SMA: alpha Smooth Muscle Actin
BMP: Bone Morphogenetic Protein
cDNA: Complementary Deoxyribonucleotide Acid
COL1A1: Collagen, type 1, Alpha 1
CDAA: Choline-Deficient L-Amino Acid-defined diet
CDAAc: Choline-Deficient L-Amino Acid-defined diet supplemented with cholesterol
CHOL: cholesterol
CSAA: Choline Supplemented L-Amino Acid-defined diet
CYPA: Cyclophilin A
DDC: 3,5-diethoxycarbonyl-1,4-dihydrocollidine
DMSO: Dimethyl sulfoxide
ELISA: Enzyme-Linked Immunosorbent Assay
EMT: Epithelial-mesenchymal transition
DTT: Dithiothreitol
FBS: Fetal Bovine Serum
FDA: Food and Drug Administration
GDF: Growth Differentiation Factors
Hh: Hedgehog
hHSC: Human Hepatic Stellate Cells
HSC: Hepatic Stellate Cells
$IC_{50}$: Half maximal Inhibitory Concentration
InMyoFib: Intestinal Myofibroblasts
MMP2: Matrix Metallopeptidase 2
MMP9: Matrix Metallopeptidase 9
µl: microliter
NHLF: Normal Human Lung Fibroblasts
NTZ: Nitazoxanide
PBC: Primary Biliary Cholangitis
PBS: Phosphate Buffer Saline
PSC: Primary Scierosing Cholangitis
qPCR: Quantitative Polymerase Chain Reaction
pMol: picomoles
rhFGF: recombinant human basic Fibroblast Growth Factor
RNA: Ribonucleic Acid
RT: Reverse Transcriptase
SmBM: Smooth Muscle cell Basal Medium
SteCGS: Stellate Cell Growth Supplement
STeCM: Stellate Cell Medium
TBA: Total Bile Acids
TGFβ1: Tumor Growth Factor beta 1
TGFBRI: TGFb type I receptor
TGFBRII: TGFb type II receptor
THBS1: Thrombospondine 1
TMB: Tetramethylbenzidine
TZ: Tizoxanide
TZG: Tizoxanide glucuronide
TZ(G): TZ or TZG FIG. 1. Nitazoxanide and its metabolite Tizoxanide inhibit TGFβ1-induced expression of α-SMA protein in human HSC Serum-deprived HSC were preincubated for 1 hour with NTZ (A) or TZ (B) before the activation with the profibrogenic cytokine TGFβ1 (1 ng/ml). After 48 hours of incubation, the expression of α-SMA was measured by ELISA. The obtained values were transformed into percentage inhibition over TGFβ1 control. Data are presented as mean (triplicates)±standard deviation (SD). Statistical analyses were performed by one-way ANOVA followed by Bonferroni post-hoc tests, using Sigma Plot 11.0 software. [*: $p<0.05$; : $p<0.01$; *: $p<0.001$ (comparison versus TGFβ1 ng/mL group)]. The curve fitting and the calculation of half maximal inhibitory concentration ($IC_{50}$) were performed with XLFit software 5.3.1.3.

Figure 2:
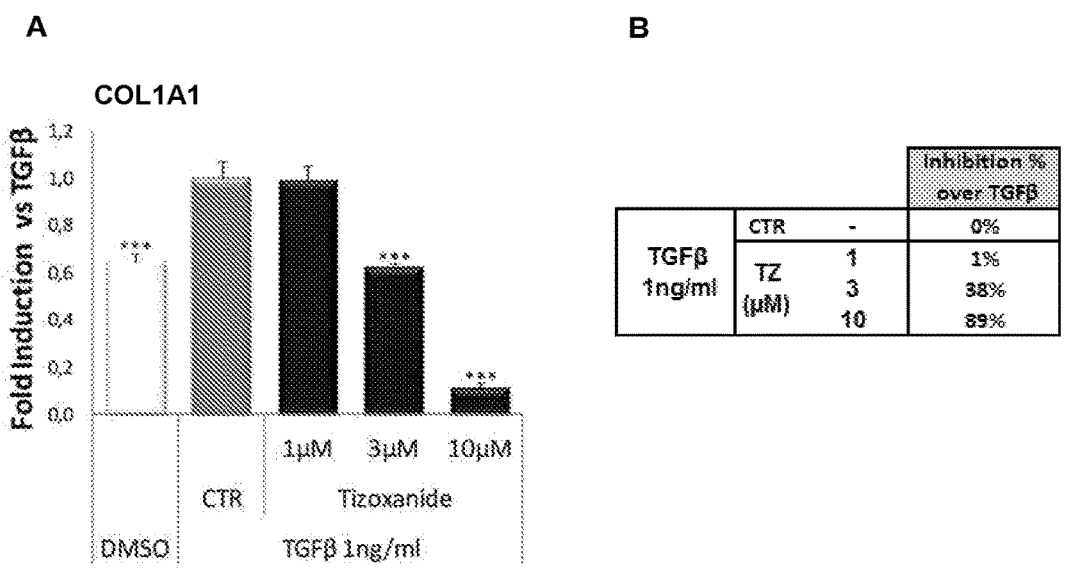

FIG. 2. Nitazoxanide and its metabolite Tizoxanide reduce COL1A1 transcripts in TGFβ1-induced human HSC Serum-deprived HSC were preincubated for 1 hour with NTZ (A) or TZ (B) before the activation with TGFβ1 (1 ng/ml). After 24 hours of incubation, the expression of COL1A1 was measured by RT-qPCR. Expression values were transformed into fold induction over TGFβ1 control. Data are presented as mean (triplicates)±standard deviation (SD). Statistical analyses were performed by one-way ANOVA followed by Bonferroni post-hoc tests, using Sigma Plot 11.0 software. [*: $p<0.05$; : $p<0.01$; *: $p<0.001$ (comparison versus TGFβ1 1 ng/mL group)].

Figure 3:
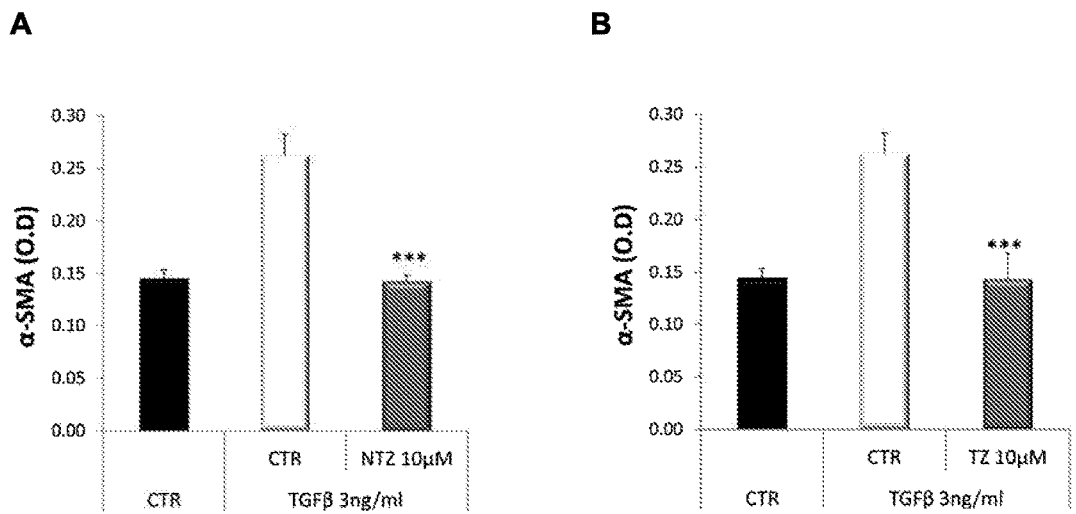

FIG. 3: NTZ (A) or TZ (B) inhibit TFGβ1-Induced expression of α-SMA protein in rat HSCs.

NTZ (A) or TZ (B) were added to serum-deprived rat HSC (rHSC) 1 hour before the activation with TGFβ1 (3 ng/ml). After 48 hours of incubation, the expression of α-SMA was measured by ELISA. The obtained values were transformed into percentage inhibition over TGFβ1 control. Data are presented as mean (triplicates) t standard deviation (SD). Statistical analyses were performed by one-way ANOVA followed by Bonferroni post-hoc tests, using Sigma Plot 11.0 software. [*: $p<0.05$; : $p<0.01$; *: $p<0.001$ (comparison versus TGFβ1 3 ng/mL group)].

Figure 4:
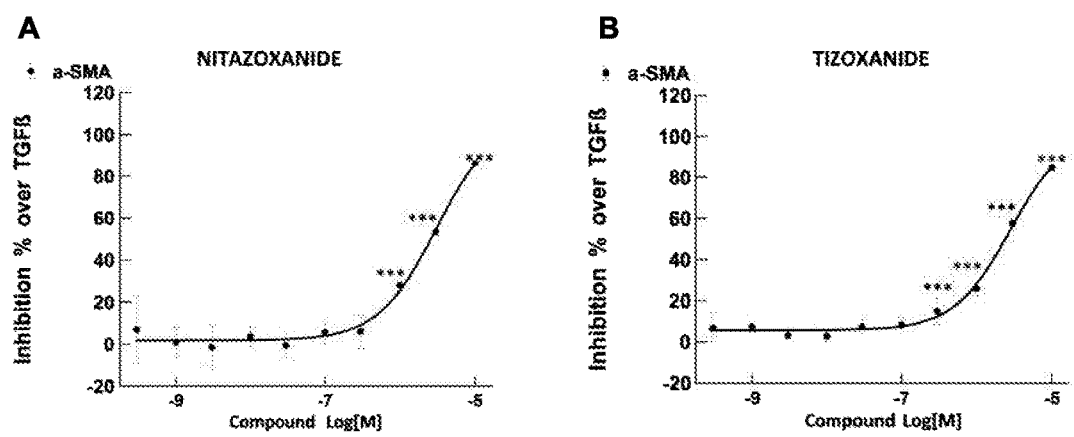

FIG. 4: NTZ (A) or TZ (B) inhibit TFGβ1-induced expression of α-SMA protein in human lung fibroblasts.

NTZ (A) or TZ (B) was added to serum-deprived lung fibroblasts (NHLF) 1 hour before the activation with TGFβ1 (1 ng/ml). After 48 hours of incubation, the expression of α-SMA was measured by ELISA. The obtained values were transformed into percentage inhibition over TGFβ1 control. Data are presented as mean (triplicates) t standard deviation (SD). Statistical analyses were performed by one-way ANOVA followed by Bonferroni post-hoc tests, using Sigma Plot 11.0 software. [*: $p<0.05$; : $p<0.01$; *: $p<0.001$ (comparison versus TGFβ1 ng/mL group)].

Figure 5:
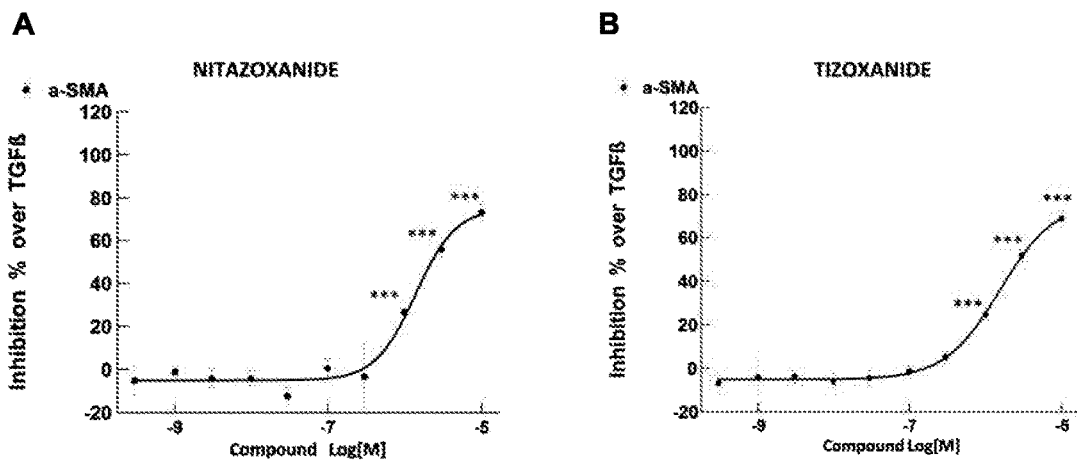

FIG. 5: NTZ (A) or TZ (B) Inhibit TFGβ1-induced expression of α-SMA protein in human cardiac fibroblasts.

NTZ (A) or TZ (B) were added to serum-deprived cardiac fibroblasts (NHCF) 1 hour before the activation with TGFβ1 (3 ng/ml). After 48 hours of incubation, the expression of α-SMA was measured by ELISA. The obtained values were transformed into percentage inhibition over TGFβ1 control. Data are presented as mean (triplicates): standard deviation (SD). Statistical analyses were performed by one-way ANOVA followed by Bonferroni post-hoc tests, using Sigma Plot 11.0 software. [*: $p<0.05$; : $p<0.01$; *: $p<0.001$ (comparison versus TGFβ1 3 ng/mL group)].

Figure 6:
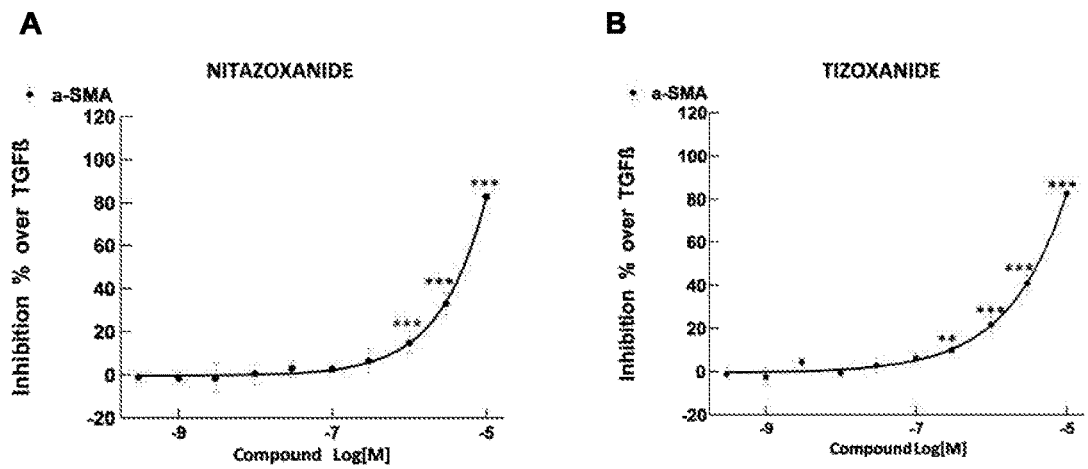

FIG. 6: NTZ (A) or TZ (B) Inhibit TFGβ1-induced expression of α-SMA protein in human intestinal fibroblasts.

NTZ (A) or TZ (B) were added to serum-deprived intestinal fibroblasts (InMyoFib) 1 hour before the activation with TGFβ1 (3 ng/ml). After 48 hours of incubation, the expression of α-SMA was measured by ELISA. The obtained values were transformed into percentage inhibition over TGFβ1 control. Data are presented as mean (triplicates) 2 standard deviation (SD). Statistical analyses were performed by one-way ANOVA followed by Bonferroni post-hoc tests, using Sigma Plot 11.0 software. [*: $p<0.05$; : $p<0.01$; *: $p<0.001$ (comparison versus TGFβ1 3 ng/mL group)].

Figure 7:
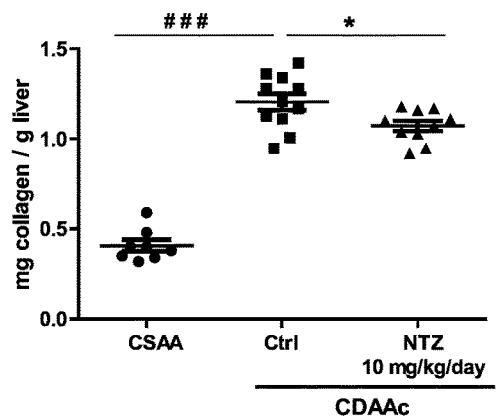

FIG. 7: The chronic oral administration of Nitazoxanide (10 mg/kg/day) prevents the CDAA-induced collagen storage in the liver of C57Bl/6J mice.

6 week-old C57BL/6 mice were fed a control (CSAA) diet, CDAA+1% CHOL (CDAAc) diet, or CDAAc diet supplemented with NTZ 10 mg/kg/day for 12 weeks. After the sacrifice, the hepatic collagen content was determined. Data are presented as mean±standard deviation (SD). Statistical analyses were performed by a student t-test using Sigma Plot 11.0 software: CSAA vs CDAAc (*: $p<0.05$; : $p<0.01$; *: $p<0.001$) and CDAAc vs NTZ 10 mg/kg/day (*: $p<0.05$; : $p<0.01$; *: $p<0.001$).

Figure 8:
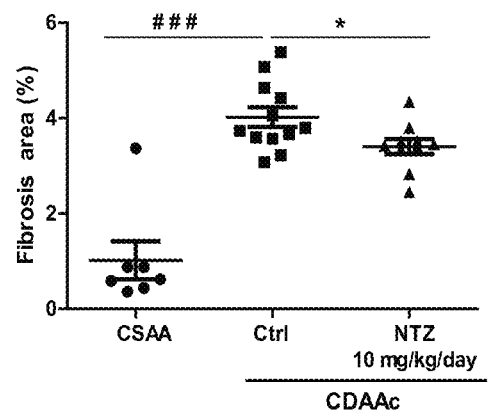

FIG. 8: The chronic oral administration of Nitazoxanide (10 mg/kg/day) prevents the CDAAc diet-induced fibrosis in the liver of C57B/6J mice.

6 week-old C57BL/6 mice were fed a control (CSAA) diet, CDAAc diet, or CDAAc diet supplemented with NTZ 10 mg/kg/day for 12 weeks. After the sacrifice, the hepatic fibrosis area was determined. Data are presented as mean±standard deviation (SD). Statistical analyses were performed by a student t-test using Sigma Plot 11.0 software: CSAA vs CDAAc (*: $p<0.05$; : $p<0.01$; *: $p<0.001$) and CDAAc vs NTZ 10 mg/kg/day (*: $p<0.05$; : $p<0.01$; *: $p<0.001$).

Figure 9:
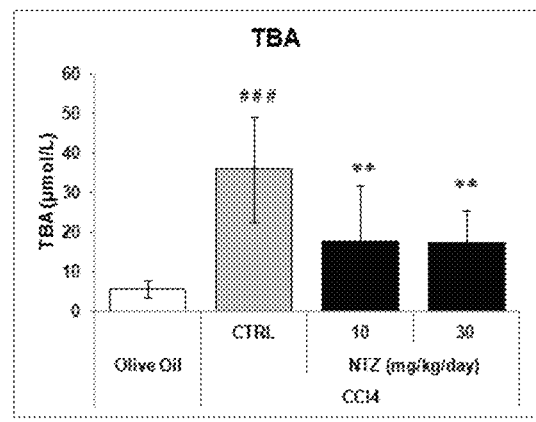

FIG. 9: The chronic oral administration of Nitazoxanide prevents CCl4-induced levels of circulating TBA concentration.

250-275 g rats were intraperitoneally injected with olive oil (ctrl group) or with CCl4 emulsified in olive oil (CCl4: olive oil 1:2 v/v, final CCl4 concentration: 2 ml/kg) twice weekly for 3 weeks. Concomitantly, the olive oil injected group was placed on control diet while the 0014 injected groups were placed on control diet or diet supplemented with NTZ 10 mg/kg/day or 30 mg/kg/day. After the sacrifice, circulating TBA concentration was determined. Data are presented as mean t standard deviation (SD). Statistical analyses were performed by a student t-test, using Sigma Plot 11.0 software: Olive Oil vs CCl4 (*: $p<0.05$; : $p<0.01$; *: $p<0.001$) and CCl4 vs NTZ (*: $p<0.05$; : $p<0.01$; *: $p<0.001$).

DETAILED DESCRIPTION OF THE INVENTION

In the experimental part of the present application, it is shown that compounds [2-[(5-nitro-1,3-thiazol-2-yl)carbamoyl]phenyl]ethanoate (Nitazoxanide) and 2-hydroxy-N-(5-nitro-2-thiazolyl)benzamide (Tizoxanide) have anti-fibrotic properties in several models of fibrosis. Moreover, it is shown that NTZ, or its active metabolite TZ, have the capacity to prevent the occurrence of altered levels of circulating bile acids in a model of liver injury, showing the ability of NTZ and TZ to treat cholestatic diseases. Accordingly, the present invention relates to novel therapeutic uses of compound NTZ or of an active metabolite thereof such as TZ or TZG.

In particular, the present invention relates to the compound NTZ or TZ(G), or a pharmaceutically acceptable salt of NTZ or TZ(G), for use in a method for the treatment of a cholestatic or fibrotic disorder. The invention relates also to a pharmaceutical composition comprising NTZ or TZ(G), or a pharmaceutically acceptable salt thereof, for use in a method for the treatment of a cholestatic or fibrotic disorder. Furthermore, the invention relates to the use of NTZ or TZ(G), or a pharmaceutically acceptable salt thereof, for the manufacture of a medicament useful for the treatment of a cholestatic or fibrotic disorder. The invention also relates to a pharmaceutical composition comprising NTZ or TZ(G), or a pharmaceutically acceptable salt thereof. The pharmaceutical composition according to the invention is useful for treating a cholestatic or fibrotic disorder.

Although the causative agents or initiating events of fibrotic disorders are quite diverse and their pathogenesis is variable, a common feature in affected tissues is the presence of large numbers of activated fibroblasts called myofibroblasts ((Rosenbloom, Mendoza et al., 2013)). Fibrotic stimulus such as TGFβ1 can induce differentiation of fibroblasts to myofibroblasts (Leask and Abraham, 2004; Leask, 2007). Myofibroblasts are metabolically and morphologically distinctive fibroblasts whose activation and proliferation play a key role in development of the fibrotic response. Furthermore, these myofibroblasts display unique biological functions including expression of proteins involved in extracellular matrix formation such as different forms of collagen, fibronectin and other ECM proteins. The induction of α-smooth muscle actin (α-SMA) expression is a recognized hallmark of quiescent fibroblast to activated myofibroblast differentiation and can be used as a physiological read-out to evaluate the potency of the drugs that interfere with the fibrotic process. Tumor Growth P factors, and especially the Tumor Growth Factor beta 1 (TGFβ1) are recognized physiological signals that induce the phenotypic transformation of fibroblasts into profibrotic myofibroblasts that express high levels of α-SMA and high levels of extracellular matrix proteins, which are then secreted and form the fibrotic scar tissue.

Moreover, it is known that the proliferation and the activation of fibroblasts is responsible for the production of several connective tissue components (for example, collagens, elastin, proteoglycans, and hyaluronan) that constitute the extracellular matrix (Kendall and Feghali-Bostwick, 2014).

Unexpectedly, NTZ but also its active metabolite TZ, reveal antifibrotic properties since these compounds dose-dependently reduced the level of α-SMA in TGFβ-induced hepatic stellate cells and in primary fibroblasts from other organs. Furthermore, treatment with NTZ or TZ also repressed collagen (Col1a1) expression in TGFβ activated rat HSC, which confirms antifibrotic properties of both molecules. The antifibrotic activity of NTZ, or its metabolite TZ was also demonstrated in vivo using a model of CDAAc-induced liver fibrosis, in which reduced hepatic collagen content and diminished fibrosis area were exemplified. Moreover. In the CCl4-Induced liver injury model, it was shown that NTZ, or its active metabolite TZ, could prevent the induction of circulating bile acid levels, which represent a marker of cholestatic diseases.

NTZ, TZ and TZG to be used according to the invention have the following Formula (I), (II) and (III) respectively:

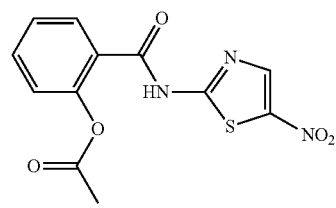

(I)

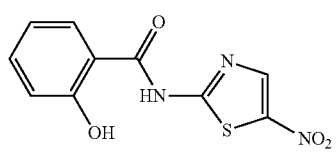

(II)

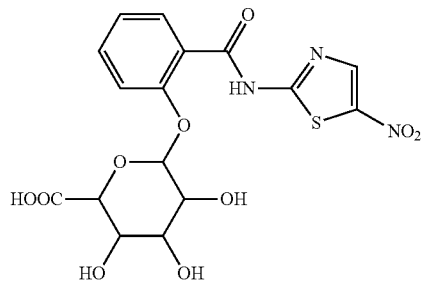

(III)

NTZ and TZ were known for their antiparasitic and antiviral activities, but the prior art does not teach that NTZ, TZ and TZG have anticholestatic and anti-fibrotic effects.

The inventors have demonstrated in a new and inventive way that these compounds have a therapeutic effect in the treatment of cholestasis or fibrosis.

Accordingly, the Invention relates to compound NTZ or TZ(G), or a pharmaceutically acceptable salt of NTZ or TZ(G), for use in a method for the treatment of a cholestatic or fibrotic disorder.

In a further aspect, the invention relates to NTZ or TZ(G), or a pharmaceutically acceptable salt of NTZ or TZ(G), for use in the inhibition of proliferation and/or activation of fibroblasts. As is known in the art, fibroblasts are responsible for the production of collagen fibers or other connective tissue components of the extracellular matrix.

According to the present invention, the terms "fibrosis", "fibrotic disease", "fibrotic disorder" and declinations thereof denote a pathological condition of excessive deposition of fibrous connective tissue in an organ or tissue. More specifically, fibrosis is a pathological process, which includes a persistent fibrotic scar formation and overproduction of extracellular matrix by the connective tissue, as a response to tissue damage. Physiologically, the deposit of connective tissue can obliterate the architecture and function of the underlying organ or tissue.

According to the present invention, the fibrosis or fibrotic disorder may be associated with any organ or tissue fibrosis. Illustrative, non-limiting examples of particular organ fibrosis include liver, gut, kidney, skin, epidermis, endodermis, muscle, tendon, cartilage, heart, pancreas, lung, uterus, nervous system, testis, penis, ovary, adrenal gland, artery, vein, colon, intestine (e.g. small intestine), biliary tract, soft tissue (e.g. medlastinum or retroperitoneum), bone marrow, joint or stomach fibrosis, in particular liver, kidney, skin, epidermis, endodermis, muscle, tendon, cartilage, heart, pancreas, lung, uterus, nervous system, testis, ovary, adrenal gland, artery, vein, colon, intestine (e.g. small intestine), biliary tract, soft tissue (e.g. mediastinum or retroperitoneum), bone marrow, joint or stomach fibrosis.

According to the present invention, the terms "cholestasis" or "cholestatic disease", or "cholestatic disorder" and declinations thereof denote a pathological condition defined by a decrease in bile flow due to impaired secretion by hepatocytes or to obstruction of bile flow through intra-or extrahepatic bile ducts. Therefore, the clinical definition of cholestasis is any condition in which substances normally excreted into bile are retained.

In a particular embodiment, the fibrotic disorder is selected in the group consisting of a liver, gut, lung, heart, kidney, muscle, skin, soft tissue (e.g. mediastinum or retroperitoneum), bone marrow, intestinal, and joint (e.g. knee, shoulder or other joints) fibrosis.

In a preferred embodiment, the fibrotic disorder is selected in the group consisting of liver, lung, skin, kidney and intestinal fibrosis.

In a more preferred embodiment of the present invention, treated fibrotic disorder is selected in the group consisting of the following non exhaustive list of fibrotic disorders: non-alcoholic steatohepatitis (NASH), pulmonary fibrosis. Idiopathic pulmonary fibrosis, skin fibrosis, eye fibrosis, endomyocardial fibrosis, mediastinal fibrosis, myelofibrosis, retroperitoneal fibrosis, progressive massive fibrosis (a complication of coal workers' pneumoconiosis), proliferative fibrosis, neoplastic fibrosis, lung fibrosis consecutive to chronic inflammatory airway disease (COPD, asthma, emphysema, smoker's lung, tuberculosis), alcohol or drug-induced liver fibrosis, liver cirrhosis, infection-induced liver fibrosis, radiation or chemotherapeutic-induced fibrosis, nephrogenic systemic fibrosis, Crohn's disease, ulcerative colitis, keloid, old myocardial infarction, scleroderma/systemic sclerosis, arthrofibrosis, some forms of adhesive capsulitis, chronic fibrosing cholangiopathies such as Primary Sclerosing Cholangitis (PSC) and Primary Biliary Cholangitis (PBC), biliary atresia, familial intrahepatic cholestasis type 3 (PFIC3), peri-implantational fibrosis and asbestosis.

According to a particular embodiment of the invention, the cholestestatic disease is selected in the group consisting of primary biliary cholangitis (PBC), primary sclerosing cholangitis (PSC). Intrahepatic Cholestasis of Pregnancy, Progressive Familial Intrahepatic Cholestasis. Biliary atresia, Cholelithiasis, Infectious Cholangitis, Cholangitis associated with Langerhans cell histiocytosis. Alagille syndrome, Nonsyndromic ductal paucity. Drug-induced cholestasis, and Total parenteral nutrition-associated cholestasis. In a preferred embodiment, the cholestatic disease is PBC or PSC, in particular PBC.

The term "treatment" or "treating" refers to the curative or preventive treatment of a cholestatic or fibrotic disorder in a subject in need thereof. The treatment involves the administration of the compound, in particular comprised in a pharmaceutical composition, to a subject having a declared disorder, i.e. to a patient, to cure, delay, reverse, or slow down the progression of the disorder, improving thereby the condition of the subject. A treatment may also be administered to a subject that is healthy or at risk of developing a cholestatic or fibrotic disorder to prevent or delay the disorder.

Therefore, according to the invention, the treatment of a fibrotic disorder involves the administration of NTZ or TZ(G), or of a pharmaceutically acceptable salt thereof, or of a pharmaceutical composition containing the same, to a subject having a declared disorder to cure, delay, reverse or slow down the progression of the disorder, thus improving the condition of the patient or to a healthy subject, in particular a subject who is at risk of developing a cholestatic or fibrotic disorder.

The subject to be treated is a mammal, preferably a human. The subject to be treated according to the invention can be selected on the basis of several criteria associated with cholestatic or fibrotic diseases such as previous drug treatments, associated pathologies, genotype, exposure to risk factors, viral infection, as well as on the basis of the detection of any relevant biomarker that can be evaluated by means of imaging methods and immunological, biochemical, enzymatic, chemical, or nucleic acid detection methods.

Synthesis of NTZ or TZ can be for example carded out as described by Rossignol and Caviar, 1975, or by any other way of synthesis known by a person skilled in the art. TZG can be, for example, synthesized according to way of synthesis known in the art such as in Wadouachi 2011. S'agit-il de A Wadouachi, J Kovensky, Synthesis of Glycosides of Glucuronic, Galacturonic and Mannuronic Acids: An Overview, Molecules, 2011, 16(5), 3933-3968.

In a particular embodiment, the treatment of a cholestatic or fibrotic disorder may comprise the administration of a combination of both NTZ and TZ(G), or of a pharmaceutically acceptable salt of NTZ and TZ(G). According to a variant of this embodiment, both NTZ and TZ(G) are comprised together in a single composition.

In another variant of this embodiment, NTZ and TZ(G) are for simultaneous, sequential or separate administration in therapy, therefore being possibly included in different compositions. In case of sequential administration, NTZ may be administered prior to the administration of TZ(G), or TZ(G) may be administered prior to NTZ administration. As such, the invention also relates to a kit-of-parts comprising (i) NTZ or a pharmaceutically acceptable salt thereof, or a pharmaceutical composition comprising NTZ or a pharmaceutically acceptable salt thereof; and (ii) TZ(G) or a pharmaceutically acceptable salt thereof, or a pharmaceutical composition comprising TZ(G) or a pharmaceutically acceptable salt thereof, for simultaneous, sequential or separate administration.

NTZ or TZ(G) can be formulated as pharmaceutically acceptable salts particularly acid or base salts compatible with pharmaceutical use. Salts of NTZ and TZ(G) include pharmaceutically acceptable acid addition salts, pharmaceutically acceptable base addition salts, pharmaceutically acceptable metal salts, ammonium and alkylated ammonium salts. These salts can be obtained during the final purification step of the compound or by incorporating the salt into the previously purified compound.

In a another aspect, the present invention concerns a pharmaceutical composition comprising a compound selected from NTZ or TZ(G), or a pharmaceutically acceptable salt of NTZ or TZ(G), for use in a method of treatment of a cholestatic or fibrotic disease.

The pharmaceutical composition comprising NTZ or TZ(G), in particular for use in a method for the treatment of a cholestatic or fibrotic disorder, can also comprise one or several pharmaceutically acceptable excipients or vehicles (e.g. saline solutions, physiological solutions, isotonic solutions, etc., compatible with pharmaceutical usage and well-known by one of ordinary skill in the art).

These compositions can also further comprise one or several agents or vehicles chosen among dispersants, solubilisers, stabilisers, preservatives, etc. Agents or vehicles useful for these formulations (liquid and/or injectable and/or solid) are particularly methylcellulose, hydroxymethylcellulose, carboxymethylcellulose, polysorbate 80, mannitol, gelatin, lactose, vegetable oils, acacia, liposomes, etc.

These compositions can be formulated in the form of injectable suspensions, syrups, gels, oils, ointments, pills, tablets, suppositories, powders, gel caps, capsules, aerosols, etc., eventually by means of galenic forms or devices assuring a prolonged and/or slow release. For this kind of formulations, agents such as cellulose, carbonates or starches can advantageously be used.

NTZ or TZ(G) may be administered by different routes and in different forms. For example, the compound(s) may be administered via a systemic way, per os, parenterally, by inhalation, by nasal spray, by nasal instillation, or by injection, such as for example intravenously, by intramuscular route, by subcutaneous route, by transdermal route, by topical route, by intra-arterial route, etc.

Of course, the route of administration will be adapted to the form of NTZ or TZ(G) according to procedures well known by those skilled in the art.

In a particular embodiment, the compound is formulated as a tablet. In another particular embodiment, the compound is administered orally.

NTZ or TZ(G), or a pharmaceutically acceptable salt thereof, is administered in a therapeutically effective amount. Within the context of the invention, the term "effective amount" refers to an amount of the compound sufficient to produce the desired therapeutic effect.

The frequency and/or dose relative to the administration can be adapted by one of ordinary skill in the art, in function of the patient, the pathology, the form of administration, etc. Typically, NTZ or TZ(G) can be administered for the treatment of a cholestatic or fibrotic disease at a dose comprised between 0.01 mg/day to 4000 mg/day, such as from 50 mg/day to 2000 mg/day, such as from 100 mg/day to 2000 mg/day; and particularly from 100 mg/day to 1000 mg/day. In a particular embodiment, the NTZ, TZ(G), or a pharmaceutically acceptable salt thereof, is administered at a dose of about 1000 mg/day (i.e at a dose of 900 to 1100 mg/day), in particular at 1000 mg/day. In a particular embodiment, NTZ, TZ(G), or a pharmaceutically acceptable salt thereof, is administered orally at a dose of about 1000 mg/day, in particular at 1000 mg/day, in particular as a tablet. Administration can be performed daily or even several times per day, if necessary. In one embodiment, the compound is administered at least once a day, such as once a day, twice a day, or three times a day. In a particular embodiment, the compound is administered once or twice a day. In particular, oral administration may be performed once a day, during a meal, for example during breakfast, lunch or dinner, by taking a tablet comprising the compound at a dose of about 1000 mg, in particular at a dose of 1000 mg. In another embodiment, a tablet is orally administered twice a day, such as by administering a first tablet comprising the compound at a dose of about 500 mg (i.e. at a dose of 450 to 550 mg), in particular at a dose of 500 mg, during one meal, and administering a second tablet comprising the compound at a dose of about 500 mg, in particular at a dose of 500 mg, during another meal the same day.

Suitably, the course of treatment with NTZ, TZ(G) or a pharmaceutically acceptable salt thereof is for at least 1 week, in particular for at least 2, 3, 4, 5, 6, 7, 8, 9, 10, 15, 20 or 24 weeks or more. In particular, the course of treatment with NTZ, TZ(G) or a pharmaceutically acceptable salt thereof is for at least 1 year, 2 years, 3 years, 4 years or at least 5 years.

In a particular embodiment, the invention relates to the treatment of a cholestatic or fibrotic disease, in particular liver fibrosis, more particularly liver fibrosis consecutive to NASH, in a patient in need thereof, comprising administering to said patient a therapeutically effective amount of NTZ or TZ(G) or of a pharmaceutically acceptable salt of NTZ or TZ(G), in particular administering NTZ at a dose of 1000 mg/day, in particular by administering a tablet containing 500 mg of NTZ twice a day, in particular during two different meals.

In a particular embodiment, the invention relates to the use of NTZ or TZ(G), or a pharmaceutically acceptable salt of NTZ or TZ(G) for the treatment of a cholestatic or fibrotic disease, in combination with at least one other therapeutically active agent with known antifibrotic activity. According to a variant of this embodiment, NTZ or TZ(G) can be combined with any antifibrotic compound such as pirfenidone or receptor tyrosine kinase inhibitors (RTKIs) such as Nintedanib, sorafenib and other RTKIs, or angiotensin II (AT1) receptor blockers, or CTGF inhibitor, or any antifibrotic compound susceptible to interfere with the TGFβ- and BMP-activated pathways including activators of the latent TGFβ complex such as MMP2, MMP9, THBS1 or cell-surface integrins. TGFβ receptors type I (TGFBRI) or type II (TGFBRII) and their ligands such as TGFβ, Activin, inhibin, Nodal, anti-Müllerian hormone, GDFs or BMPs, auxiliary co-receptors (also known as type III receptors), or components of the SMAD-dependent canonical pathway including regulatory or inhibitory SMAD proteins, or members of the SMAD-independent or non-canonical pathways including various branches of MAPK signaling, TAK1, Rho-like GTPase signaling pathways, phosphatidylinosltol-3 kinase/AKT pathways. TGFβ-induced EMT process, or canonical and non-canonical Hedgehog signaling pathways including Hh ligands or target genes, or any members of the WNT, or Notch pathways which are susceptible to influence TGFβ signaling.

Thus, the invention also relates to a pharmaceutical composition comprising a compound selected from NTZ or TZ(G), or a pharmaceutically acceptable salt of NTZ or of TZ(G), in combination with at least one therapeutically active agent with known antifibrotic activity selected from pirfenidone or receptor tyrosine kinase inhibitors (RTKIs) such as Nintedanib, sorafenib and other RTKIs, or angiotensin II (AT1) receptor blockers, or CTGF inhibitor, or antifibrotic compound susceptible to interfere with the TGFβ- and BMP-activated pathways including activators of the latent TGFβ complex such as MMP2, MMP9, THBS1 or cell-surface integrins, TGFβ receptors type I (TGFBRI) or type II (TGFBRII) and their ligands such as TGFβ, Activin, inhibin, Nodal, anti-Müllerian hormone, GDFs or BMPs, auxiliary co-receptors (also known as type III receptors), or components of the SMAD-dependent canonical pathway including regulatory or inhibitory SMAD proteins, or members of the SMAD-independent or non-canonical pathways including various branches of MAPK signaling, TAK1, Rho-like GTPase signaling pathways, phosphatidylinositol-3 kinase/AKT pathways. TGFβ-induced EMT process, or canoninal and non-canonical Hedgehog signaling pathways including Hh ligands or target genes, or any members of the WNT, or Notch pathways which are susceptible to influence TGFβ signaling, for use in a method for treating a fibrotic disorder.

In another particular embodiment, other classes of molecules that could also be combined with NTZ or TZ(G) include JAK/STAT inhibitors, or other anti-inflammatory and/or immunosuppressant agents. A non exhaustive list of these agents includes but is not limited to glucocorticolds, NSAIDS, cydophosphamide, nitrosoureas, folic acid analogs, purine analogs, pyrimidine analogs, methotrexate, azathioprine, mercaptopurine, ciclosporin, myriocin, tacrolimus, sirolimus, mycophenolic acid derivatives, fingolimod and other sphingosine-1-phosphate receptor modulators, monoclonal and/or polyclonal antibodies against such targets as proinflammatory cytokines and proinflammatory cytokine receptors, T-cell receptor, integrins. Other classes of molecules that could also be combined with NTZ or TZ(G) include molecules that could potentially enhance the exposure or the effect of NTZ or TZ(G).

In another particular embodiment, the invention relates to a combination of NTZ, TZ(G) or a pharmaceutically acceptable salt thereof with at least one other therapeutically active agent with known antifibrotic activity, or with JAK/STAT inhibitors, or other anti-inflammatory and/or immunosuppressant agents. The combination may be in the form of a single pharmaceutical composition comprising the different active ingredients, including NTZ, TZ(G), or a pharmaceutically acceptable salt thereof. In a variant, the combination is a kit of parts comprising NTZ, TZ(G), or a pharmaceutically acceptable salt thereof, and another active ingredient such as another anti-fibrotic agent, a JAK/STAT inhibitor, or another anti-inflammatory or immunosuppressant agent. Said kit of parts may be for simultaneous, separate or sequential administration for the treatment of a cholestatic or fibrotic disorder In another embodiment, compound NTZ or TZ(G), or a combination of NTZ and TZ(G), is administered as the sole active ingredient. Accordingly, the invention also relates to a pharmaceutical composition comprising a compound selected from NTZ or TZ(G), or a pharmaceutically acceptable salt of NTZ or of TZ(G), or a mixture thereof, for use in a method for treating a cholestatic or fibrotic disorder, wherein said compound(s) is(are) the only active ingredient(s) in the composition In a further embodiment, the present invention provides methods of treating cholestatic or fibrotic diseases comprising the administration of NTZ or TZ(G), or a pharmaceutically acceptable salt of NTZ or TZ(G), in particular in the form of a pharmaceutical composition containing NTZ or TZ.

In another aspect, the invention relates to a kit-of-parts comprising:
  Nitazoxanide or a pharmaceutically acceptable salt of Nitazoxanide: and
  Tizoxanide or a pharmaceutically acceptable salt of Tizoxanide.

The compounds of the kit of parts of the invention are administered simultaneously, separately or sequentially for the treatment of a fibrotic disorder.

In another embodiment, the invention provides a method of treating a cholestactic and/or fibrotic diseases comprising administering twice daily to a patient in need thereof having a cholestatic or fibrotic disease (in particular to a NASH patient or to a patient having a liver fibrosis) a tablet containing 500 mg of NTZ, in particular during a meal (such as during breakfast, lunch or dinner).

The invention is further described with reference to the following, non-limiting, examples.

EXAMPLES

Materials & Methods

Compounds were dissolved in dimethyl sulfoxide (DMSO, Fluka cat #41640). Nitazoxanide (INTERCHIM cat #RQ550U) and Tizoxanide (INTERCHIM cat #RP253) were obtained commercially.

hHSC Culture

The human primary hepatic stellate cells (hHSC) (Innoprot) were cultured in STeCM medium (ScienCell cat #5301) that was supplemented with 2% fetal bovine serum (FBS, ScienCell cat #0010), 1% penicillin/streptomycin (ScienCell cat #0503) and stellate cell growth supplement (SteCGS; ScienCell cat #5352). Cell culture flasks were coated with Poly-L Lysine (Sigma cat # P4707) for a better adherence.

Activation of hHSC with TGF-β1

The human primary hepatic stellate cells (hHSC) (Innoprot) were cultured under standard conditions, as described above. The cells were subsequently plated at a density of $7 \times 10^4$ cells/well into 24-well plates for gene expression studies, and at a density of $2 \times 10^4$ cells/well into 96-well plates for the measure of α-SMA by ELISA. The next day, cell culture medium was removed, and cells were washed with PBS (Invitrogen cat #14190). hHSC were deprived for 24 hours in serum-free and SteCGS-free medium. For the treatments with NTZ or TZ, the serum-deprived hHSC were preincubated for 1 hour with the compounds followed by the addition of the profibrogenic stimuli TGFβ1 (PeproTech cat #100-21, 1 ng/mL) in serum-free and SteCGS-free medium for an additional 24 or 48 hour period (the timepoint is indicated in the figure legends). At the end of treatment, cells were washed with PBS (Invitrogen, cat #14190) before the addition of 50 µl of lysis buffer (CelLytic™ MT reagent; Sigma #C3228). Plates were then incubated for 30 min on ice using a plate shaker, before storage at −20° C.

Activation of Rat HSC with TGFβ1:

The rat primary hepatic stellate cells (rHSC) (Innoprot) were cultured in STeCM medium (ScienCell cat #5301) that was supplemented with 2% fetal bovine serum (FBS, ScienCell cat #0010), 1% penicillin/streptomycin (ScienCell cat #0503) and stellate cell growth supplement (SteCGS; ScienCell cat #5352). For the activation experiments with TGFβ1, the rHSC were plated at a density of $10 \times 10^3$ cells per well in 96-well plates. The next day, cell culture medium was removed, and cells were washed with PBS (Invitrogen cat #14190). rHSC were deprived for 24 hours in serum-free and SteCGS-free medium. For the treatments with NTZ or TZ, the serum-deprived rHSC were preincubated for 1 hour with the compounds followed by addition of the profibrogenic stimuli TGFβ1 (PeproTech cat #100-21, 3 ng/mL) in serum-free and SteCGS-free medium for an additional 48 hour period. At the end of treatment, cells were washed with PBS (Invitrogen, cat #14190) before the addition of 50 µl of lysis buffer (CelLytic™ MT reagent; Sigma #C3228). Plates were then incubated for 30 min on ice using a plate shaker, before storage at −20° C.

Activation of NHLF with TGFβ1

The Normal Human Lung Fibroblasts (NHLF) (Lonza) were cultured in Fibroblast Basal Medium (FBM) (Lonza cat # CC-3131) that was supplemented with FGM-2 SingleQuots™ Kit (Lonza cat # CC-3132). The complete medium contains 2% fetal bovine serum. For the activation experiments with TGFβ1, the NHLF were plated at a density of $5 \times 10^3$ cells per well in 96-well plates. The next day, cell-culture medium was removed, and cells were washed with PBS (Invitrogen cat #14190). NHLF were deprived for 24 hours in serum-free, insulin-free and rhFGF-B-free medium. For the treatments with NTZ or TZ, the serum-deprived NHLF were preincubated for 1 hour with the compounds followed by addition of the profibrogenic stimuli TGFβ1 (PeproTech cat #100-21, 1 ng/mL) in serum-free, insulin-free and rhFGF-B-free medium for an additional 48 hour period. At the end of treatment, cells were washed with PBS (Invitrogen, cat #14190) before the addition of 50 µl of lysis buffer (CelLytic™ MT reagent; Sigma #C3228). Plates were then incubated for 30 min on ice using a plate shaker, before storage at −20° C.

Activation of NHCF-V with TGFβ1:

The Normal Human Cardiac Fibroblasts (ventricle) (NHCF-V) (Lonza) were isolated from normal adult heart tissue. Cells were cultured in Fibroblast Basal Medium (FBM) (Lonza cat #CC-3131) that was supplemented with FGM™-3 BulletKit™ kit (Lonza cat # CC-4525). The complete medium contains 10% fetal bovine serum. For the activation experiments with TGFβ1, the NHCF-V were plated at a density of $6 \times 10^3$ cells per well in 96-well plates. The next day, cell-culture medium was removed, and cells were washed with PBS (Invitrogen cat #14190). NHCF were deprived for 24 hours in serum-free, insulin-free and rhFGF- B-free medium. For the treatments with NTZ or TZ, the serum-deprived NHCF were preincubated for 1 hour with the compounds followed by addition of the profibrogenic stimulus TGFβ1 (PeproTech cat #100-21, 3 ng/mL) in serum-free, insulin-free and rhFGF-B-free medium for an additional 48 hour period. At the end of treatment, cells were washed with PBS (Invitrogen, cat #14190) before the addition of 50 µl of lysis buffer (CelLytic™ MT reagent; Sigma #C3228). Plates were then incubated for 30 min on ice using a plate shaker, before storage at −20° C.

Activation of InMyoFib with TGFβ1:

The Human Intestinal Myofibroblasts (InMyoFib) (Lonza) were cultured in Smooth Muscle Cell Basal Medium (SmBM-2TM) (Lonza cat # CC-3181) that was supplemented with SmGMTM-2 BulletKit™ (Lonza cat # CC-4149). The complete medium contains 5% fetal bovine serum. For the activation experiments with TGFβ1, the inMyoFib were plated at a density of $10 \times 10^3$ cells per well in 96-well plates. The next day, cell-culture medium was removed, and cells were washed with PBS (Invitrogen cat #14190). InMyoFib were deprived for 24 hours in serum-free, insulin-free and rhFGF-B-free medium. For the treatments with NTZ or TZ, the serum-deprived InMyoFib were preincubated for 1 hour with the compounds followed by addition of the profibrogenic stimuli TGFβ1 (PeproTech cat #100-21, 3 ng/mL) in serum-free, insulin-free and rhFGF-B-free medium for an additional 48 hour period. At the end of treatment, cells were washed with PBS (Invitrogen, cat #14190) before the addition of 50 µl of lysis buffer (CelLytic™ MT reagent; Sigma #C3228). Plates were then incubated for 30 min on ice using a plate shaker, before storage at −20° C.

α-SMA ELISA

The level of α-SMA was measured using a Sandwich ELISA. Briefly, the wells of an ELISA plate were first coated with the capture antibody (mouse monoclonal anti-ACTA2, Abnova) at 4° C. overnight. After 3 washes in PBS+0.2% Tween 20, a blocking solution consisting of PBS+0.2% BSA was added for one hour followed by another washing cycle. The cell lysates were transferred into the wells for binding to the capture antibody for a period of 2h at room temperature. After the washing procedure, the detection antibody (biotinylated mouse monoclonal anti-ACTA2, Abnova) was added for 2 hours at room temperature followed by 3 washes. For the detection, an HRP-conjugated Streptavidin (R&D Systems cat # DY998) was first applied for 30 min at room temperature. After washing, the HRP substrate TMB (BD, #555214) was added and incubated for 7 min at room temperature in the dark. Upon oxidation, TMB forms a water-soluble blue reaction product that becomes yellow with addition of sulfuric acid (solution stop), enabling accurate measurement of the intensity at 450 nm using a spectrophotometer. The developed color is directly proportional to the amount of α-SMA present in the lysate.

Gene Expression

Total RNA was isolated using Nucleospin® 96 RNA (Macherey Nagel) following manufacturer's instructions. Total RNA (500 ng for in vitro samples) were reverse transcribed into cDNA using M-MLV RT (Moloney Murine Leukemia Virus Reverse Transcriptase) (Invitrogen cat #28025) in IX RT buffer (Invitrogen). 1 mM DTT (Invitrogen), 0.18 mM dNTPs (Promega), 200 ng pdN6 (Amersham) and 30 U of RNase inhibitor (Promega). Quantitative PCR was then carried out using the MyiQ Single-Color Real-Time PCR Detection System (Biorad). Briefly, the PCR reactions were performed in 96-WP format in 25 ul of total volume containing 1 µL of reverse transcription reaction, 0.5 µL of reverse and forward primers (10 pmol each), and 12.5 µl of 2× iQ SYBR Green Supermix (BioRad. 1725006CUST). The sequences of primers are depicted in the table 1

TABLE 1

| Human Primers | |
|---|---|
| Primer name | Sequence (5'→3') |
| 36B4 forward | CATCTCAACATCTCCCCCTTCTCC (SEQ ID NO: 1) |
| 36B4 reverse | GGGAAGGTGTAATCCGTCTCCACAG (SEQ ID NO: 2) |
| COL1A1 forward | AGGCGAACAAGGTGACAGAG (SEQ ID NO: 3) |
| COL1A1 reverse | GCCAGGAGAACCAGCAGAG (SEQ ID NO: 4) |

Expression levels were normalized using the expression of 36B84 gene as a reference in human samples.

For each gene, the standard curves were drawn by selecting the best points (at least three points) In order to have PCR reaction efficiency close to 100% and a correlation coefficient close to 1. Expression levels were determined using the standard curve equation for both the housekeeping gene and the target gene (taking into account the specific PCR efficiency of each target gene).

Evaluation of NTZ in a Chronic CDAAc Diet-Induced Liver Fibrosis Model

The antifibrotic effect of NTZ was assessed in a murine model of CDAAc diet-induced experimental liver fibrosis. 6 week-old C57BL/6 mice were fed for 12 weeks a control (CSAA) diet, CDAAc diet, or CDAAc diet supplemented with NTZ 10 mg/kg/day for 12 weeks.

The body weight and the food intake were monitored twice per week. On the last day of treatment, mice were sacrificed after a 6h fasting period. The liver was rapidly excised for biochemical and histological studies.

All animal procedures were performed according to standard protocols and in accordance with the standard recommendations for the proper care and use of laboratory animals.

Evaluation of NTZ in CCl4-Induced Liver Damage Model

The antifibrotic effect of NTZ was assessed in a rat model of CCl4 induced liver injury.

OFA S; Dawley rats (initial body weight 250-275 g) were randomized according to their body weight into 4 groups and treated for 3 weeks. The rats were intraperitoneally injected with olive oil (ctrl group) or with CCl4 emulsified in olive oil (CCl4:olive oil 1:2 v/v, final CCl4 concentration: 2 ml/kg) twice weekly. Concomitantly, the olive oil injected group was placed on control diet while the CCl4 injected groups were placed on control diet or diet supplemented with NTZ. 2 regimen containing NTZ were prepared corresponding respectively to an exposure of 10, or 30, mg/kg/day. The last day of treatment, the rats were sacrificed after a 6h fasting period. Blood samples were collected and the serum was isolated for biochemical analyses.

Evaluation of NTZ in the DDC Model of Cholestasis:

C57BL/6 mice will be fed for 8 weeks a 0.1% DDC-supplemented diet, or 0.1% DDC-supplemented diet containing NTZ 100 mg/kg/day, or a standard mouse diet (Ssniff). The last day of treatment, the mice will be sacrificed after a 6h fasting period. Blood samples will be taken for biochemical analyses and the liver will be rapidly excised for biochemical and histological studies.

Evaluation of NTZ in a Chronic CCl4-Induced Liver Fibrosis Model 9 week-old C57BL/6 mice will be placed on control diet or diet supplemented with NTZ for 6 weeks. 2 regimen containing NTZ will be prepared corresponding respectively to an exposure of NTZ 30, or 100 mg/kg/day. Concomitantly, and for the total duration of 6 weeks, the mice will be treated 3 times a week with CCl4 dissolved in olive oil or vehicle by oral gavage. The amount of C014 will be progressively increased from 0.875 ml/kg to 2.5 ml/kg. The last day of treatment, the mice will be sacrificed after a 6h fasting period. Blood samples will collected for biochemical analyses of serum. The liver will be rapidly excised for biochemical, histological and expression studies.

Histology

Tissue Embedding and Sectioning:

The liver slices were first fixed for 12 hours in a solution of 4% formalin. The, liver pieces were then washed 30 minutes in PBS, and dehydrated in ethanol solutions (successive baths at 70, 80, 95 and 100% ethanol). The liver pieces were incubated in three different baths of Xylene (Sigma-Aldrich cat #534056), followed by two baths in liquid paraffin (56° C.). Liver pieces were then put into racks that were gently filled with Histowax® to completely cover the tissue.

The paraffin blocks containing the tissue pieces were removed from the racks and stored at room temperature. The liver blocks were cut into 3 µm slices.

Picrosirius Red Staining

Liver sections were deparaffinized, rehydrated and incubated for 15 minutes in a solution of Fast Green FCF 0.1% (Sigma-Aldrich, cat # F7258) before rinsing in a bath of 0.5% acetic acid (Panreac, cat #131008.1611). The liver sections were rinsed in water and incubated for 30 minutes in a solution of 0.1% sirius red (Direct Red 80, Fluka cat #43665) in saturated aqueous picric acid (Sigma-Aldrich cat # P6744). The liver sections were finally dehydrated, and mounted using the CV Mount medium (Leica, cat #14046430011).

Histological Examinations

The identity of the liver specimen was blinded from the examiner. Virtual slides were generated using the Pannoramic 250 scanner from 3D Histech. Using Quant Center software (3D Histech, including Pattern Quant and Histo Quant modules), collagen-stained areas were quantified. Briefly, Pattern Quant was used to detect relevant tissue structure and to measure the surface. Then, Histo Quant was used to detect the stained collagen content and for the measurement of total area and percentages, based on a color threshold method. The fibrosis area was expressed as the percentage of collagen surface over the whole tissue.

Measurement of Hepatic Collagen Content

The hepatic collagen content was determined using the appropriate QuickZyme kit (Total collagen assay, cat # QZB-totcol2). The assay is based on the detection of hydroxyproline, which is a non-proteinogenic amino acid mainly found in the triple helix of collagen. Thus, hydroxyproline in tissue hydrolysates can be used as a direct measure of the amount of collagen present in the tissue (without discrimination between procollagen, mature collagen and collagen degradation products).

Complete hydrolysis of tissue samples in 6M HCl at 95° C. is required before dosing the hydroxyproline. The assay results in the generation of a chromogen with a maximum absorbance at 570 nm. Results are expressed as mg of collagen/g of liver.

Evaluation of NTZ in the BDL Model

Surgical bile duct ligation will be performed on rats in order to induce an extrahepatic cholestasis and subsequently liver fibrosis. After a 2 week recovery period, animals will be treated with NTZ at 30 or 100 mg/kg/day for one or two weeks. The last day of treatment, the mice will be sacrificed after a 6h fasting period. Blood samples will be collected for biochemical analyses of serum. The liver will be rapidly excised for biochemical, histological & expression studies.

Measurement of Plasmatic Concentration of Total Bile Acids

The plasmatic concentration of Total Bile Acids (TBA) was determined using the appropriate Randox kit for the Daytona automated analyzer (Randox, cat #BI 3863). In the presence of Thio-NAD, the enzyme 3-α hydroxysteroid dehydrogenase (3-α HSD) converts bile acids to 3-keto steroids and Thio-NADH. The reaction is reversible and 3-α HSD can convert 3-ketosteroids and Thio-NADFH-to bile acids and Thio-NAD. In the presence of excess NADH, the enzyme cycling occurs efficiently and the rate of formation of Thio-NADH is determined by measuring specific change of absorbance at 405 nm. Results are expressed in pmol/L.

RESULTS AND CONCLUSIONS

The abnormal persistence of differentiated myofibroblasts is a characteristic of many fibrotic diseases. Following liver injury, quiescent HSC undergo a process of activation that is characterized by a differentiation into (α-SMA)-positive myofibroblasts. In an attempt to find new antifibrotic molecules, a library of FDA-approved drugs was phenotypically screened in a model of human HSC activated with the profibrogenic cytokine TGFβ1. The levels of α-SMA, a hallmark of fibrotic lesions, were used to evaluate the potency of the drugs to interfere with the fibrotic process. The screening campaign led to the identification of nitazoxanide (NTZ), which dose-dependently reduced the level of α-SMA in TGFβ-induced HSCs. Overall, NTZ exhibited an $IC_{50}$ comprised between 0.1 and 3 µM (FIG. 1A). Since it is known that NTZ is rapidly hydrolyzed into an active metabolite tizoxanide (TZ) (Broekhuysen, Stockis et at, 2000), this metabolite was also evaluated for its antifibrotic activity in HSC. TZ showed a profile similar to the parent drug with an $IC_w$ comprised between 0.1 and 3 µM (FIG. 1B). Other markers of TGFβ stimulation were reduced by both compounds including the extracellular matrix collagen 1A1 (COL1A1) (FIG. 2). Toxicity assays confirmed that the reduced levels of α-SMA were not due to toxicity or apoptosis of HSC (data not shown).

NTZ and TZ also reduced α-SMA levels in TGFβ-activated HSC derived from rat (FIG. 3). In addition, the antifibrotic potential of NTZ and TZ was extended to fibroblasts derived from other tissues, including normal human lung fibroblasts (NHLF) (FIG. 4), normal human cardiac fibroblasts (FIG. 5) and human Intestinal myofibroblasts (InMyoFib) (FIG. 6). In all these models of fibrosis, NTZ and TZ showed significant antifibrotic effects at a concentration of 1 µM.

In vivo efficacy of NTZ was assessed in a CDAA cholesterol diet-induced experimental liver fibrosis model. The chronic oral administration of Nitazoxanide 10 mg/kg/day demonstrated antifibrotic properties reflected by significantly lower hepatic collagen content (FIG. 7) and reduced hepatic fibrosis area by histological examination (FIG. 8).

In the in vivo model of CCl₄-induced liver injury, NTZ prevented the pathological increase of circulating TBA concentration (FIG. 09), which is a marker associated with cholestasis (Chang 2013) In conclusion, the applicant has discovered unexpected antifibrotic and anticholestatic activities for the antiparasitic agent NTZ. These results demonstrate that NTZ and/or its active metabolite TZ can provide therapeutic benefits in cholestatic diseases and multiple types of fibrotic diseases.

REFERENCES

Broekhuysen, J., A. Stockis, et al. (2000). "Nitazoxanide: pharmacokinetics and metabolism in man." *Int J Clin Pharmacol Ther* 38(8): 387-394.

de Carvalho, L. P. S., C. M. Darby, et al. (2011). "Nitazoxanide disrupts membrane potential and intrabacterial pH homeostasis of *Mycobacterium tuberculosis.*" *ACS Med. Chem. Lett.* 2 (Copyright (C) 2015 American Chemical Society (ACS). All Rights Reserved): 849-854.

Di Santo, N. and J. Ehrisman (2014). "A functional perspective of nitazoxanide as a potential anticancer drug." *Mutat. Res., Fundam. Mol. Mech. Mutagen.* 768 (Copyright (C) 2015 American Chemical Society (ACS). All Rights Reserved): 16-21.

Dubreuil, L., I. Houcke, et al. (1996). "In vitro evaluation of activities of nitazoxanide and tizoxanide against anaerobes and aerobic organisms." *Antimicrob. Agents Chemother.* 40 (Copyright (C) 2015 American Chemical Society (ACS). All Rights Reserved): 2266-2270.

Finegold, S. M., D. Molitoris, et al. (2009). "Study of the in vitro activities of rifaximin and comparator agents against 536 anaerobic intestinal bacteria from the perspective of potential utility in pathology involving bowel flora." *Antimicrob. Agents Chemother.* 53 (Copyright (C) 2015 American Chemical Society (ACS). All Rights Reserved): 281-286.

Fox, L. M. and L. D. Saravolatz (2005). "Nitazoxanide: a new thiazolide antiparasitic agent." *Clin. Infect. Dis.* 40 (Copyright (C) 2015 American Chemical Society (ACS). All Rights Reserved): 1173-1180.

Hemphill, A., J. Mueller, et al. (2006). "Nitazoxanide, a broad-spectrum thiazolide anti-infective agent for the treatment of gastrointestinal infections." *Exert Opin. Pharmacother.* 7 (Copyright (C) 2015 American Chemical Society (ACS). All Rights Reserved): 953-964.

Hoffman. P. S. G. Sisson, et al. (2007). "Antiparasitic drug nitazoxanide inhibits the pyruvate oxidoreductases of *Helicobacter pylori*, selected anaerobic bacteria and parasites, and *Campylobacter jejuni.*" *Antimicrob. Agents Chemother.* 51 (Copyright (C) 2015 American Chemical Society (ACS). All Rights Reserved): 868-876.

Kendall, R. T. and C. A. Feghall-Bostwick (2014). "Fibroblasts in fibrosis: novel roles and mediators." *Front Pharmacol* 5: 123.

Leask, A. (2007). "TGFbeta, cardiac fibroblasts, and the fibrotic response." *Cardiovasc Res* 74(2): 207-212.

Leask. A. and D. J. Abraham (2004). "TGF-beta signaling and the fibrotic response." *FASEB J* 18(7): 816-827.

Megraudd, F., A. Occhialini, et al. (1998). "Nitazoxanide, a potential drug for eradication of *Helicobacter pylori* with no cross-resistance to metronidazole." *Antimicrob. Agents Chemother.* 42 (Copyright (C) 2015 American Chemical Society (ACS). All Rights Reserved): 2836-2840.

Pankuch, G. A. and P. C. Appelbaum (2006). "Activities of tizoxanide and nitazoxanide compared to those of five other thiazolides and three other agents against anaerobic species." *Antimicrob. Agents Chemother.* 50 (Copyright (C) 2015 American Chemical Society (ACS). All Rights Reserved): 1112-1117.

Rosenbloom, J., F. A. Mendoza, et al. (2013). "Strategies for anti-fibrotic therapies." *Bochim Biohys Acta* 1832(7): 1088-1103.

Rossignol, J.-F. (2014). "Nitazoxanide: A first-in-class broad-spectrum antiviral agent." *Antiviral Res.* 110 (Copyright (C) 2015 American Chemical Society (ACS). All Rights Reserved): 94-103.

Rossignol, J. F. and R. Cavier (1975). 2-Benzamido-5-nitrothiazoles, S.P.R.L. Phavic, Belg. 11 pp.

Rossignol. J. F. and H. Malsonneuve (1984). "Nitazoxanide in the treatment of *Taenia saginata* and *Hymenolepis nana* infections." *Am J Trop Med Hyg* 33 (Copyright (C) 2015 U.S. National Library of Medicine): 511-512.

---

The invention claimed is:

1. A method for treating intestinal fibrosis comprising administering to a subject in need thereof a therapeutic effective amount of a compound selected in the group consisting of Nitazoxanide (NTZ), Tizoxanide (TZ), and a pharmaceutically acceptable salt of NTZ or TZ.

2. The method according to claim 1, wherein the compound is administered orally.

3. The method according to claim 1, wherein the compound is administered in an amount comprised between 100 mg/day and 2000 mg/day.

4. The method according to claim 1, wherein the compound is administered in the form of a pharmaceutical composition providing prolonged or slow release of the compound.

5. The method according to claim 1, wherein intestinal fibrosis is small intestine fibrosis.

6. A method for treating intestinal fibrosis comprising administering to a subject in need thereof a therapeutic effective amount of nitazoxanide.

7. The method according to claim 6, wherein nitazoxanide is administered orally.

8. The method according to claim 6, wherein nitazoxanide is administered in an amount comprised 100 mg/day and 2000 mg/day.

9. The method according to claim 6, wherein nitazoxanide is administered in the form of a pharmaceutical composition providing prolonged or slow release of nitazoxanide.

10. The method according to claim 6, wherein intestinal fibrosis is small intestine fibrosis.

* * * * *